United States Patent
Singh et al.

(10) Patent No.: US 11,358,129 B2
(45) Date of Patent: Jun. 14, 2022

(54) PROCESS FOR THE PRODUCTION OF ETHYLENE GLYCOL AND HETEROGENEOUS CATALYST COMPOSITION

(71) Applicant: Avantium Knowledge Centre B.V., Amsterdam (NL)

(72) Inventors: Jagdeep Singh, Amsterdam (NL); Paula Dekker, Amsterdam (NL); Jan Cornelis Van Der Waal, Amsterdam (NL); Benjamin McKay, Amsterdam (NL)

(73) Assignee: Avantium Knowledge Centre B.V., Amsterdam (NL)

( * ) Notice: Subject to any disclaimer, the term of this patent is extended or adjusted under 35 U.S.C. 154(b) by 95 days.

(21) Appl. No.: 16/977,748

(22) PCT Filed: Mar. 14, 2019

(86) PCT No.: PCT/EP2019/056512
§ 371 (c)(1),
(2) Date: Sep. 2, 2020

(87) PCT Pub. No.: WO2019/175365
PCT Pub. Date: Sep. 19, 2019

(65) Prior Publication Data
US 2020/0406237 A1 Dec. 31, 2020

(30) Foreign Application Priority Data
Mar. 14, 2018 (NL) .................................. 2020585

(51) Int. Cl.
*C07C 29/00* (2006.01)
*C07C 31/20* (2006.01)
(Continued)

(52) U.S. Cl.
CPC ............... *B01J 23/96* (2013.01); *B01J 21/18* (2013.01); *B01J 23/462* (2013.01);
(Continued)

(58) Field of Classification Search
None
See application file for complete search history.

(56) References Cited

U.S. PATENT DOCUMENTS

2011/0313210 A1   12/2011   Kaines et al.

FOREIGN PATENT DOCUMENTS

| CN | 102643165 B | 7/2014 |
| WO | 2017055289 A1 | 4/2017 |

OTHER PUBLICATIONS

Machine translation of Patent No. CN102643165B, Jun. 2, 2014, pp. 8-12 (Year: 2014).*

(Continued)

*Primary Examiner* — Medhanit W Bahta
(74) *Attorney, Agent, or Firm* — Suiter Swantz pc llo (57) ABSTRACT

The invention relates to a process for the production of ethylene glycol including the steps of:
(i) reacting, in a reactor, at a temperature in the range from equal to or more than 170° C. to equal to or less than 270° C., at least a portion of a carbohydrate source in the presence of hydrogen, a solvent, a homogeneous catalyst, which homogeneous catalyst contains tungsten, and a heterogeneous catalyst, which heterogeneous catalyst contains one or more transition metals from groups 8, 9 and 10 of the Periodic Table of the Elements, yielding ethylene glycol and a spent heterogeneous catalyst;
(ii) regenerating the spent heterogeneous catalyst by removing at least a portion of deposited tungsten species from the spent heterogeneous catalyst, yielding a regenerated heterogeneous catalyst; and
(iii) using at least a portion of the regenerated heterogeneous catalyst as heterogeneous catalyst in the reaction of step (i).

(Continued)

The invention further relates to a regenerated heterogeneous catalyst composition obtainable therein.

14 Claims, 1 Drawing Sheet

(51) Int. Cl.
  *B01J 23/96* (2006.01)
  *B01J 21/18* (2006.01)
  *B01J 23/46* (2006.01)
  *B01J 23/652* (2006.01)
  *B01J 37/06* (2006.01)
  *C07C 29/136* (2006.01)
(52) U.S. Cl.
  CPC ........... *B01J 23/6527* (2013.01); *B01J 37/06* (2013.01); *C07C 29/00* (2013.01); *C07C 29/136* (2013.01); *C07C 31/20* (2013.01); *C07C 31/202* (2013.01)

(56) References Cited

OTHER PUBLICATIONS

International Search Report and Written Opinion dated Jun. 18, 2019 for PCT/EP2019/056512.
Written Opinion of the International Preliminary Examining Authority dated Feb. 24, 2020 for PCT/EP2019/056512.

* cited by examiner

PROCESS FOR THE PRODUCTION OF ETHYLENE GLYCOL AND HETEROGENEOUS CATALYST COMPOSITION

FIELD OF THE INVENTION

The present invention relates to a process for the production of ethylene glycol. The present invention further relates to a heterogeneous catalyst composition.

BACKGROUND TO THE INVENTION

Alkylene glycols, such as ethylene glycol, are bulk chemicals that can be used in a wide variety of applications. They can be used as monomer in the preparation of polyesters, such as poly(ethylene terephthalate), poly(ethylene naphthenate) or poly(ethylene furandicarboxylate), but ethylene glycol can also be used for example in heat transfer media and anti-freeze compositions.

Recently, increased efforts are being made to produce alkylene glycols from sustainable resources, such as carbohydrates. By enabling the preparation of alkylene glycols, such as ethylene glycol, from sustainable resources, the dependence of fossil fuel resources is advantageously reduced.

In their article titled "From microcrystalline cellulose to hard- and softwood-based feedstocks: their hydrogenolysis to polyols over a highly efficient ruthenium-tungsten catalyst", published on 20 Mar. 2015 in vol. 17 (5) of Green Chemistry, Fabičovicová et al describe the hydrogenolysis of cellulosic materials to ethylene glycol with a bifunctional catalyst, Ru/W/AC, comprising ruthenium and tungsten on activated carbon. The bifunctional Ru/W/AC catalyst was prepared by impregnating an activated carbon material with an aqueous solution of ammonium metatungstate hydrate followed by drying. Hereafter the pre-catalyst W/AC was obtained, that was impregnated with an aqueous solution of ruthenium nitrosyl nitrate followed by drying and reduction in a hydrogen flow, giving the final Ru/W/AC catalyst. Recycling tests of the Ru/W/AC catalyst were performed in order to test the stability of this catalyst. The bifunctional Ru/W/AC catalyst was used for the hydrogenolysis of cellulose during a period of 3 hours at 493 K (corresponding to about 220° C.). Hereafter the product solution was filtered and the catalyst was washed with deionized water and dried at 383 K under an air atmosphere. After drying the catalyst was scraped from the filter, re-weighed and recovered for the next run. Fabičovicová et al. state that the Ru/W/AC catalyst maintained its stability during six cycles. In the last (seventh) run, i.e. after 21 hours, the yield of polyols decreased to 46.4% and the product distribution differed significantly.

To elucidate the performance of the heterogeneous Ru/W/AC catalyst in the light of the interplay of soluble hydrogen tungsten bronze (HxWO3), the reaction with Ru/W/AC catalyst containing 36.7% of tungsten was compared with a reaction with Ru/AC and tungsten acid (H2WO4). It was concluded that the yield of ethylene glycol was greater if the heterogeneous Ru/W/AC catalyst was used. The use of a combination of Ru/AC and H2WO4 resulted in a lower production of ethylene glycol and a higher production of sorbitol. Hence, Fabičovicová et al. focused on using a heterogeneous bifunctional Ru/W/AC catalyst.

U.S. Pat. No. 4,072,628 describes a process for regenerating a supported ruthenium catalyst, especially a ruthenium-containing zeolite catalyst, which has been used to convert a carbohydrate to a polyhydric alcohol in the presence of hydrogen under elevated pressure at a temperature in the range of about 100° C. to about 200° C. The process comprises separating the catalyst from the reaction medium and contacting the catalyst with a dilute aqueous solution of a water soluble acid, such as sulfuric acid, hydrochloric acid and phosphoric acid. The ruthenium is present as the free metal finely dispersed on the surfaces of the zeolite, which serves both as a support and as an acid catalyst for the hydrolysis of polysaccharides. U.S. Pat. No. 4,072,628 teaches the need for a certain acidity and mentions that alkali metal ions such as sodium are detrimental to catalyst activity. In the examples illustrating the re-use of the catalyst for the conversion of carbohydrates, however, mostly sorbitol is produced and no alkylene glycols such as ethylene glycol or propylene glycol are prepared.

WO2016/114661 describes a continuous process for preparing ethylene glycol from a carbohydrate source by reaction of the carbohydrate source with hydrogen. In the process hydrogen, the carbohydrate source and a liquid diluent are continuously fed into a continuous stirred tank reactor (CSTR) wherein a catalyst system is present. The described catalyst system comprises a tungsten compound and at least one hydrogenolysis metal selected from the groups 8, 9 or 10 of the Periodic Table of the Elements. WO2016/114661 describes that continuously a product mixture comprising ethylene glycol and diluent is removed from the continuous stirred tank reactor; and further continuously or periodically at least a tungsten compound is added to the continuous stirred tank reactor. WO2016/114661 further explains that if and to the extent that any hydrogenolysis catalyst is removed from the CSTR during the reaction, such maybe complemented by periodical or continuous addition thereof to the CSTR.

In its examples WO2016/114661 illustrates interesting results with selectivity's towards ethylene glycol as high as about 60 wt. %, calculated as the weight percentage in the reactor effluent divided by the amount of grams glucose being introduced into the CSTR. The runtime in the experiments, however, did not exceed 7 hours. WO2016/114661 mentions that humins may be formed which accelerate the deactivation of the catalyst and that accordingly the glucose conversion is decreased over time. CN 102643165 B (in machine translation) discloses a continuous reaction process for catalyzing the hydrocracking of sugars to produce ethylene glycol and 1,2 propylene glycol in a reactor. The soluble catalyst components are partially recycled back to the reactor. US 2011/313210 relates to a catalytic process for generating at least one polyol from a feedstock comprising cellulose is performed in a continuous manner. The process involves, contacting, continuously, hydrogen, water, and a feedstock comprising cellulose, with a catalyst to generate an effluent stream comprising at least one polyol, water, hydrogen, and at least one co-product. The water, hydrogen, and at least one co-product are separated from the effluent stream and recycled to the reaction zone. The polyol is recovered from the effluent stream. The process may further comprise separating catalyst from the effluent stream and recycling the catalyst to the reaction zone. WO 2017/055289 discloses a process for the preparation of glycols from a saccharide-containing feedstock using a catalyst component with retro-aldol catalytic capabilities and a first hydrogenation catalyst comprising an element selected from groups 8, 9 and 10 of the periodic table. The process may further comprise separating catalyst from the effluent stream and recycling the catalyst to the reaction zone.

It would be an advancement in the art to provide a process for the preparation of ethylene glycol from a carbohydrate source, that would allow for a prolonged runtime with an economically interesting selectivity towards ethylene glycol.

SUMMARY OF THE INVENTION

Such a process has been obtained with the process according to the invention. Accordingly the present invention provides a process for the preparation of ethylene glycol from a carbohydrate source including the steps of:
(i) reacting, in a reactor, at a temperature in the range from equal to or more than 170° C. to equal to or less than 270° C., at least a portion of a carbohydrate source in the presence of hydrogen, a solvent, a homogeneous catalyst, which homogeneous catalyst contains tungsten, and a heterogeneous catalyst, which heterogeneous catalyst contains one or more transition metals from groups 8, 9 and 10 of the Periodic Table of the Elements, yielding ethylene glycol and a spent heterogeneous catalyst;
(ii) regenerating the spent heterogeneous catalyst by removing at least a portion of deposited tungsten species from the spent heterogeneous catalyst, yielding a regenerated heterogeneous catalyst; and
(iii) using at least a portion of the regenerated heterogeneous catalyst as heterogeneous catalyst in the reaction of step (i).

The above process advantageously allows one to operate the process for the production of ethylene glycol for a prolonged period of time with an economically interesting selectivity towards ethylene glycol. The process according to the invention may advantageously have a runtime of equal to or more than 50 hours and even equal to or more than 100 hours.

WO2016/114661 mentioned the believe that hexavalent tungsten may be reduced to pentavalent tungsten in the reducing atmosphere that is created in the reaction zone by means of the presence of hydrogen and carbohydrates. Without wishing to be bound to any kind of theory, inventors now believe that the heterogeneous catalyst, comprising one or more transition metals from groups 8, 9 and 10 of the Periodic Table of the Elements, is important in catalyzing such reduction of hexavalent tungsten to pentavalent tungsten. It is further believed that, if operated for a prolonged period of time, an increasing amount of tungsten species can deposit onto the surface of the heterogeneous catalyst, increasingly preventing the heterogeneous catalyst from catalyzing the hydrogenation of alkylene glycol precursors to alkylene glycol, resulting in a decrease in selectivity towards ethylene glycol.

The discovery of this previously unrecognized problem caused the inventors to recognize the need for the removal of deposited tungsten species from the heterogeneous catalyst.

The invention further relates to a heterogeneous catalyst composition obtained or obtainable by the above process. It was found that the regenerated heterogeneous catalyst was novel and inventive on its own. The present invention therefore also provides an, suitably isolated, heterogeneous catalyst composition containing:
one or more transition metals from groups 8, 9 and 10 of the Periodic Table of the Elements, supported on a carrier; and
one or more tungsten species deposited onto the transition metal(s), wherein the weight ratio of weight tungsten to the total weight of transition metal, all calculated on metal basis, is equal to or lower than 10:1.

BRIEF DESCRIPTION OF THE DRAWINGS

The invention is illustrated by the following FIGURES.

DETAILED DESCRIPTION OF THE INVENTION

Preferably step (i) is preceded by a step wherein the carbohydrate source, the solvent, hydrogen and the homogeneous catalyst are provided to the reactor. If not already present (for example in a fixed bed reactor) also a heterogeneous catalyst, which heterogeneous catalyst contains one or more transition metals from groups 8, 9 and 10 of the Periodic Table of the Elements, can be provided to such reactor.

By a carbohydrate source is herein understood a source of carbohydrates. The carbohydrate source can be selected from a variety of sources. Preferably, the carbohydrate source comprises one or more carbohydrates chosen from the group consisting of polysaccharides, oligosaccharides, disaccharides, monosaccharides and mixtures thereof.

Suitable examples may include, preferably sustainable, sources of carbohydrates such as cellulose, hemicellulose, starch, sugars, such as sucrose, mannose, arabinose, fructose, glucose and mixtures thereof. Carbohydrate sources that contain the above carbohydrates may include dextrose syrups, maltose syrups, sucrose syrups, glucose syrups, crystalline sucrose, crystalline glucose, wheat starch, corn starch, potato starch, cassava starch, and other carbohydrate containing streams, for example paper pulp streams, wood waste, paper waste, agricultural waste, cellulosic residues recovered from municipal waste, paper, cardboard, sugar cane, sugar beet, wheat, rye, barley, corn, rice, potatoes, cassava, other agricultural crops and combinations thereof. These streams may require pre-treatment to extract the carbohydrates (for example wet milling in the case or corn) or to remove components that interfere with the current process such as basic fillers (for example the removal of calcium carbonate in waste paper). In this way the process according to the invention can use natural sources, but can also be used to upgrade and usefully re-use waste streams. Preferably, the carbohydrates in the carbohydrate source are chosen from the group consisting of cellulose, hemicellulose, starch, glucose, sucrose, glucose-oligomers and combinations thereof. Since cellulose presents difficulties that are absent in other carbohydrate sources, the carbohydrate source is most preferably selected from the group consisting of starch, hemicelluloses and hemicellulosic sugars, glucose and mixtures thereof. Most preferably the carbohydrate source comprises or consists of glucose, fructose, sucrose or a combination thereof.

Suitably, the carbohydrate source can be provided to the reactor together with at least part of a solvent. More preferably, the carbohydrate source is partially or wholly dissolved in such a solvent. Preferences for such solvent are provided below. The solvent can for example be an aqueous medium, an organic medium including alkylene glycols, or a mixture containing water, diols and/or other polyols. Many carbohydrates are soluble in water or a mixture containing water, diols and/or other polyols. The carbohydrate source can also be provided to the reactor in the form of a slurry. Examples of such slurries include aqueous mixtures of water and hemicellulose, hemicellulosic sugars, glucose and/or starch.

The present process advantageously allows for the provision to the reactor of a very concentrated feed stream containing the carbohydrate source. When employing such a concentrated feed stream the process economics benefit. Such a feed stream may suitably comprise the carbohydrate source and a solvent, for example water and/or diols and/or other polyols.

Preferably the carbohydrate source is provided to the reactor by a feed stream containing the carbohydrate source and a solvent, wherein such feed stream preferably contains in the range from equal to or more than 1.0 wt. % (weight percent), preferably equal to or more than 2.0 wt. %, more preferably equal to or more than 5.0 wt. %, even more preferably equal to or more than 10.0 wt. %, and still more preferably equal to or more than 20.0 wt. % of carbohydrate source to equal to or less than 90.0 wt. %, preferably equal to or less than 70.0 wt. % and more preferably equal to or less than 50.0 wt. % of carbohydrate source, based on the total weight of the carbohydrate source and solvent. A feed stream containing carbohydrate source within this concentration range can suitably be easily transported. The feed stream can also consist of only (100 wt. %) carbohydrate source.

For practical purposes the carbohydrate source can be provided to the reactor by a feed stream containing the carbohydrate source and a solvent, wherein such feed stream contains in the range from equal to or more than 2.0 wt. %, more preferably equal to or more than 10.0 wt. %, to equal to or less than 50.0 wt. %, more preferably to equal to or less than than 30.0 wt. % of carbohydrate source, based on the total weight of the carbohydrate source and solvent. Most preferably a feed stream containing or consisting of carbohydrate source and solvent is provided to the reactor, wherein such feed stream contains in the range of equal to or more than 20.0 wt. % to equal to or less than 50.0 wt. %, more preferably equal to or less than 30.0 wt. % of carbohydrate source, based on the total weight of the carbohydrate source and solvent. It is believed that such a feedstream containing equal to or more than 20.0 wt. % of carbohydrate source can make the process economically more attractive. Such solvent may comprise any of the solvents mentioned below, but is preferably water. Most preferably the carbohydrate source is provided to the reactor by a feed stream containing the carbohydrate source and water, wherein such feed stream contains in the range from equal to or more than 2.0 wt. % to equal to or less than 30.0 wt. % of carbohydrate source, based on the total weight of the carbohydrate source and water.

Preferably the carbohydrate source is continuously or periodically added to the reactor. Preferably the carbohydrate source is provided to the reactor under a blanket of inert gas, such as nitrogen.

Solvent can be supplied as part of a feed stream comprising carbohydrate source, as described above. It is also possible for the solvent to be provided to the reactor separately or independently from the carbohydrate source.

Preferably a feed stream is used containing the carbohydrate source and solvent. The concentration of carbohydrate source in such a feed stream may suitably be adjusted such that sufficient solvent is provided to the reactor.

The solvent is preferably selected from the group consisting of water and optionally, one or more of the above-mentioned organic solvents, such as diols and/or other polyols; and mixtures thereof. Suitably the solvent can be a mixture of water and one or more organic solvents. Alkanols are preferred as organic solvent. Such alkanols can be mono-alkanols, preferably water-miscible mono-alkanols, such as methanol, ethanol, propanol, butanol and mixtures thereof. For the process according to the invention, such light mono-alkanols are, however, less preferred. The alkanol can also be a water-miscible diol or other polyol, e.g. ethylene glycol, propylene glycol, butylene glycol, glycerol, xylytol, sorbitol or erythritol. By a diol is herein understood an organic compound comprising two hydroxyl groups. Preferably the solvent comprises an alkylene glycol. Examples of preferred alkylene glycols include ethylene glycol, propylene glycol, butylene glycol and mixtures thereof. The use of alkylene glycol is especially advantageous as it has been found that diols and/or polyols, including alkylene glycols, facilitate the dissolution of tungsten or a tungsten compound into the solvent, thereby promoting the catalytic activity of the tungsten or tungsten compound. It has further been found that the selectivity of the reaction to alkylene glycols is enhanced by the use of alkylene glycol as component in the solvent. Without wishing to be bound by any theory, it is believed that tungsten forms complexes with alkylene glycol whereby the conversion to by-products is reduced. Moreover, the use of an alkylene glycol as solvent does not involve the introduction of an extraneous reagent into the reaction mixture, which represents a further advantage. Preferably the solvent comprises or consists of water, one or more alkylene glycols, one or more alkanols, optionally one or more polyols, or a mixture of two or more thereof.

Preferably the solvent is continuously or periodically added to the reactor. At the same time a portion of the solvent may be continuously or periodically withdrawn from the reactor.

The hydrogen can be provided to the reactor as substantially pure hydrogen. Alternatively, the hydrogen may be supplied in the form of a mixture of hydrogen and an inert gas. The inert gas can suitably be selected from nitrogen, argon, helium, neon and mixtures thereof. The volume ratio of hydrogen to the inert gas may vary between wide ranges. Suitably, the volume ratio is not very low, since the reaction proceeds well when the hydrogen partial pressure is sufficiently high. Accordingly, the volume ratio between hydrogen and the inert gas may be from 1:1 to 1:0.01. More preferably, only hydrogen is used as gas in the process according to the invention.

The total pressure during the reaction comprises the vapour pressure of the solvent and the reactants at the temperature and pressure applied, in addition to the partial pressure of the hydrogen and, if present, the partial pressure of any inert gas. Preferences for the total pressure are provided below.

Hydrogen can suitably be provided via a dip tube, for example a dip tube close to an agitator, or via a distributor, for example a sparger, to the reactor. Via such dip tube or distributor and optionally via one or more stirring mechanisms, hydrogen can be dissolved in the reaction mixture. Preferably the hydrogen is continuously or periodically added to the reactor.

The homogeneous catalyst and heterogeneous catalyst are together herein also referred as the catalyst system.

The homogeneous catalyst contains tungsten and is herein also referred to as tungsten-comprising homogenous catalyst.

The tungsten can be present as elemental tungsten or as a tungsten compound. Such a tungsten compound can for example be a tungstic acid or a tungstate salt. The homogeneous catalyst can suitably contain one or more tungsten compounds. The tungsten or tungsten compound(s) can suitably be dissolved in the reaction mixture. Preferably, the tungsten has an oxidation state of at least +2. More preferably the tungsten has an oxidation state of +4, +5 or +6. When dissolved in the solvent, or respectively the reaction mixture, the dissolved tungsten or dissolved tungsten compound may form complexes with (other) components of the solvent, or respectively the reaction mixture.

The homogeneous catalyst provided to the reactor can be freshly made homogeneous catalyst or recycled homogeneous catalyst. Freshly made homogeneous catalyst is herein also referred to as "virgin" homogeneous catalyst. Such virgin homogeneous catalyst is preferably selected from the group consisting of tungstic acid ($H_2WO_4$) and tungstate compounds, such as tungstic salts, for example comprising at least one Group 1 or 2 element, for example sodium tungstate ($Na_2WO_4$) or potassium tungstate ($K_2WO_4$) or for example comprising ammonium tungstate. It is also possible to use a combination of one or more of these.

Suitably the homogeneous catalyst provided to the reactor can contain recycled homogeneous catalyst or a combination of virgin homogeneous catalyst and recycled homogeneous catalyst. That is, the homogeneous catalyst provided to the reactor in the current invention can contain or consist of recycled tungsten species recovered, directly or indirectly (for example via a distillation), from the effluent of the reactor.

Any recycled homogeneous catalyst may contain tungsten as a complex with components from the solvent in which such homogeneous catalyst may be dissolved. The recycled homogeneous catalyst may therefore suitably comprise tungsten in a form derived from a precursor tungsten compound, such as the above virgin homogeneous catalyst, as originally provided.

Preferably the homogeneous catalyst contains a tungsten compound or tungsten derived from a tungsten compound, wherein such tungsten compound is selected from the group consisting of tungstic acid ($H_2WO_4$), tungsten bronze (present as $H_xWO_3$ or $M_xWO_3$, wherein x is a variable smaller than 1 (<1) and M is a metal, for example an alkali or alkali earth metal), ammonium tungstate, ammonium metatungstate, ammonium paratungstate, tungstate compounds comprising at least one Group 1 or 2 element, metatungstate compounds comprising at least one Group 1 or 2 element, paratungstate compounds comprising at least one Group 1 or 2 element, tungsten oxide ($WO_3$), heteropoly compounds of tungsten, and combinations thereof. Tungstic acid ($H_2WO_4$), tungsten bronze ($H_xWO_3$) and tungstate compounds comprising at least one Group 1 or 2 element, for example sodium tungstate ($Na_2WO_4$) or potassium tungstate ($K_2WO_4$), are preferred. Most preferably the homogeneous catalyst contains a tungsten compound or tungsten derived from a tungsten compound, wherein such tungsten compound is sodium tungstate and/or tungstic acid and/or tungsten bronze.

It has been found that the catalytic activity of the tungsten or tungsten compound advantageously increases if the tungsten or suitably the tungsten compound is dissolved. Preferably the homogeneous catalyst is continuously or periodically added to the reactor. Preferably such homogeneous catalyst that is continuously or periodically added contains tungsten that has an oxidation state of at least +2. Preferably the homogeneous catalyst is chosen from the group consisting of tungstic acid ($H_2WO_4$), tungsten bronze ($H_xWO_3$), sodium tungstate, a dissolved tungstate ion, a dissolved metatungstate ion and a dissolved paratungstate ion.

As the tungsten can be present in so many forms, the tungsten and/or tungsten compounds are herein also referred to as tungsten species. By a tungsten species is herein understood any compound containing or consisting of tungsten element in any kind of form or oxidation state.

When (partly) oxidized, the tungsten species is herein also referred to as tungstate species. By a tungstate species is herein understood any compound comprising a tungsten-oxide bond. Examples of tungstate species include tungsten dioxide and tungsten trioxide and tungsten bronze.

Preferably the homogeneous catalyst is dissolved in a solvent. Such solvent can be any solvent as described above. The composition of the solvent may vary during the process. Whilst the reaction is carried out in the reactor, the solvent may be formed by the reaction mixture itself.

The amount of tungsten, calculated as metal, that is provided to the reactor is preferably such that the concentration thereof in the reactor is maintained substantially constant. By substantially constant is herein understood that the difference between the highest and the lowest amounts of tungsten, calculated as metal, does not vary more than 10% from the average amount of tungsten in the reactor. Preferably the process according to the invention is a continuous or semi-continuous process. Preferably a tungsten species is continuously or periodically added to the reactor. At the same time a portion of the tungsten species inside the reactor may be continuously or periodically withdrawn from the reactor, suitably via the reactor product stream. Whereas it is feasible to add tungsten periodically, it is preferred to provide for a continuous addition of tungsten to the reactor. More preferably tungsten is added to the reactor as a solution of tungsten species in the solvent.

Preferably the concentration of tungsten species in the reaction mixture during the reaction ranges from equal to or more than 0.01 wt. % (corresponding to 100 parts per million by weight (ppmw)) to equal to or less than 10.0 wt. % of tungsten (calculated as tungsten metal), based on the total weight of the reaction mixture. More preferably the concentration of tungsten species in the reaction mixture during the reaction ranges from equal to or more than 0.01 wt. %, preferably equal to or more than 0.05 wt. %, to equal to or less than 5.0 wt. %, to equal to or less than 1.0 wt. %, or even equal to or less than 0.5 wt. %, of tungsten (calculated as tungsten metal), based on the total weight of the reaction mixture.

The heterogeneous catalyst contains one or more transition metals from groups 8, 9 and 10 of the Periodic Table of the Elements. The transition metal(s) can be selected from a wide range of transition metals. Preferably the one or more transition metal(s) is/are selected from the group consisting of Cu, Fe, Ni, Co, Pt, Pd, Ru, Rh, Ir, Os and combinations thereof. More preferably the one or more transition metal(s) is/are selected from the group consisting of Ni, Pd, Pt, Ru, Rh, Ir and combinations thereof. Most preferred are nickel, ruthenium and combinations thereof. It has been found that these metals give good yields. The transition metal can suitably be present in its metallic form or as its hydride or oxide or as another compound. As explained below, it is also possible for the transition metal to be present in a partly tungstated form.

The heterogeneous catalyst preferably comprises one or more transition metals from groups 8, 9 and 10 of the Periodic Table of the Elements, supported on a carrier. The carrier may be selected from a wide range of known carrier materials. Suitable carriers include activated carbon (also referred to as "active carbon"), silica, zirconia, alumina, silica-alumina, titania, niobia, iron oxide, tin oxide, zinc oxide, silica-zirconia, zeolitic aluminosilicates, titanosilicates, magnesia, silicon carbide, clays and combinations thereof. By activated carbon is herein understood an amorphous form of carbon with a surface area of at least 800 m²/g. Such activated carbon suitably has a porous structure. Most preferred carriers are activated carbon, silica, silica-alumina and alumina. Even more preferably, the catalyst comprises ruthenium and/or nickel as the transition metal and activated carbon as the carrier. Most preferably the heterogeneous catalyst contains ruthenium and/or nickel supported on activated carbon. Most preferably the heterogeneous catalyst contains ruthenium, preferably supported on activated carbon.

The heterogeneous catalyst can for example be present as an emulsion, a slurry or as a fixed bed. Preferably the heterogeneous catalyst comprises in the range from equal to or more than 1.0 wt. %, more preferably equal to or more than 2.0 wt. %, still more preferably equal to or more than 5.0 wt. %, to equal to or less than 50.0 wt. %, more preferably equal to or less than 20.0 wt. % of transition metal, on the basis of the total weight of transition metal and carrier.

It is possible for the heterogeneous catalyst to comprise more than one metal. Suitably, the heterogeneous catalyst can comprise at least one noble metal, selected from the group consisting of Pd, Pt, Ru, Rh and Ir, in combination with a second transition metal selected from the group of transition metals from groups 8, 9 or 10 of the Periodic Table of the Elements. The heterogeneous catalyst can for example comprise a combination of metals, for example Ni/Ir, Ni/Pt, Ni/Pd, Ni/Ru, Ru/Ir, Ru/Pt or Ru/Pd.

As explained in more detail below, it is believed that during the reaction tungsten species can become deposited onto the heterogeneous catalyst. Therefore at least a portion of the heterogeneous catalyst can contain tungsten in addition to the one or more transition metals from groups 8, 9 and 10 of the Periodic Table of the Elements.

Preferably the process according to the invention is a continuous or semi-continuous process. In such a continuous or semi-continuous process a slurry of heterogeneous catalyst, for example together with solvent, can be periodically or continuously added to the reactor. Preferably such a slurry of heterogeneous catalyst comprises in the range from equal to or more than 5 wt. % to equal to or less than 90 wt. %, more preferably equal to or less than 70 wt. %, most preferably equal to or less than 50 wt. % of heterogeneous catalyst, based on the total weight of such slurry. Preferably such a slurry is a slurry of heterogeneous catalyst in water and/or an alkylene glycol, for example ethylene glycol and/or propylene glycol and/or butylene glycol, and/or a polyol.

The weight ratio of the total amount of tungsten species (calculated on metal basis) provided to the reactor, to the transition metal (calculated on metal basis) provided to the reactor, may vary between wide ranges. The weight ratio of weight tungsten to the total weight of transition metal, all calculated on metal basis, as provided to the reactor preferably ranges from equal to or more than 1:3000 to equal to or less than 50:1 (tungsten metal:transition metal weight ratio (wt/wt)). More preferably the weight ratio of weight tungsten to the total weight of transition metal, all calculated on metal basis, as provided to the reactor preferably ranges from equal to or more than 1:200 to equal to or less than 50:1 (tungsten metal:transition metal weight ratio (wt/wt)).

The weight ratio of the total amount of tungsten species (calculated on metal basis) present in the reactor, to the transition metal (calculated on metal basis) present in the reactor, may also vary between wide ranges. The weight ratio of weight tungsten to the total weight of transition metal, all calculated on metal basis, as present in the reactor preferably ranges from equal to or more than 1:3000 to equal to or less than 50:1 (tungsten metal:transition metal weight ratio (wt/wt)). More preferably the weight ratio of weight tungsten to the total weight of transition metal, all calculated on metal basis, as present in the reactor preferably ranges from equal to or more than 1:200 to equal to or less than 50:1 (tungsten metal:transition metal weight ratio (wt/wt)).

More preferably the molar ratio of moles tungsten to the total moles transition metal, all calculated on metal basis, as provided to the reactor, preferably ranges from equal to or more than 1:1 to equal to or less than 25:1, more preferably from equal to or more than 2:1 to equal to or less than 20:1 (tungsten metal:transition metal mole ratio (moles/moles)).

Also the molar ratio of moles tungsten to the total moles transition metal, all calculated on metal basis, as present in the reactor, preferably ranges from equal to or more than 1:1 to equal to or less than 25:1, more preferably from equal to or more than 2:1 to equal to or less than 20:1 (tungsten metal:transition metal mole ratio (moles/moles)).

The concentration of tungsten species, calculated as tungsten metal, based on the weight of carbohydrate source introduced into the reactor, preferably ranges from equal to or more than 0.1 wt. %, more preferably from equal to or more than 1 wt. % to equal to or less than 50 wt. %, more preferably equal to or less than 35 wt. %. Even more preferably the concentration of tungsten species, calculated as tungsten metal, based on the weight of carbohydrate source introduced into the reactor, preferably ranges from equal to or more than 0.2 wt. %, even more preferably from equal to or more than 2 wt. % to equal to or less than 25 wt. %.

The concentration of transition metal introduced per hour into the reactor, based on the weight of carbohydrate source introduced per hour into the reactor, preferably ranges from equal to or more than 0.001 wt. %, more preferably from equal to or more than 0.01 wt. %, even more preferably from equal to or more than 0.1 wt. %, more preferably from equal to or more than 0.2 wt. % to equal to or less than 2.0 wt. %, more preferably to equal to or less than 1.0 wt. %.

Step (i) suitably comprises reacting, in a reactor, at a temperature in the range from equal to or more than 170° C. to equal to or less than 270° C., at least a portion of the carbohydrate source in the presence of hydrogen, the solvent, the homogeneous catalyst, which homogeneous catalyst contains tungsten, and the heterogeneous catalyst, which heterogeneous catalyst contains one or more transition metals from groups 8, 9 and 10 of the Periodic Table of the Elements. Such step (i) suitably yields ethylene glycol and a spent heterogeneous catalyst.

The reactor can be any type of reactor known to be suitable for the production of ethylene glycol from a carbohydrate source. Preferably the reactor is an agitated or mixed reactor. The reactor can for example be a slurry reactor, an ebulated bed reactor, a fluidized bed reactor, a bubble reactor, an external recycle loop reactor, a continuous stirred tank reactor (CSTR) or another type of mechanically agitated reactor. Most preferably the reactor is a continuously stirred tank reactor (CSTR). The use of a CSTR is very advantageous for the present process as the CSTR provides an excellent means for diluting the eventual concentration of the carbohydrate in the CSTR, whereas the feed stream may comprise a high concentration of carbohydrate. At the same time the alkylene glycols that are produced by the reaction of the carbohydrate provide a medium wherein tungsten species may be dissolved, thereby benefitting the catalytic activity of the tungsten catalyst component. Hence, it is preferred that the homogeneous catalyst contains or consists of tungsten species dissolved a solvent, which solvent comprises or consists of one or more alkylene glycols.

The reactor can also be a plug flow reactor. Heterogeneous catalyst can be provided to such a plug flow reactor as a slurry or it can suitably be present as a fixed bed.

The residence time in the reactor may vary. Preferably the mean residence time of the carbohydrate source in the reactor is at least 1 min. (By mean residence time is herein understood the average time spent by a material flowing at a volumetric rate "u" through a volume "V", as further explained in the handbook "Modeling of Chemical Kinetics and Reactor Design" by A. Kayode Coker, published in 2001 by Butterworth Heinemann). Preferably the mean residence time of the carbohydrate source is in the range from equal to or more than 1 minutes to equal to or less than 6 hours, more preferably from equal to or more than 3 minutes to 2 hours, most preferable in the range from equal to or more than 5 minutes to equal to or less than 45 minutes. If the carbohydrate source reacts quickly, however, the mean residence time may also be shorter than 5 minutes and even shorter than 3 minutes.

If a feed stream to the reactor is used containing in the range of equal to or more than 20.0 wt. % of carbohydrate source, based on the total weight of the carbohydrate source and solvent, the mean residence time of the carbohydrate source in the reactor is preferably equal to or more than 5 minutes, more preferably equal to or more than 10 minutes, and preferably equal to or less than 2 hours, more preferably equal to or less than 45 minutes. It is believed that such a longer mean residence time can advantageously assist to convert a feedstream with a higher concentration of carbohydrate source.

Preferably the process is a continuous process. Preferably a continuous process is operated at a weight hourly space velocity (WHSV), expressed as the mass of carbohydrate source per mass of transition metal, expressed as metal, per hour, in the range of 0.01 to 100 hr$^{-1}$, preferably from 0.05 to 10 hr$^{-1}$. For practical purposes a WHSV in the range between 0.5 to 2.0 hr$^{-1}$ can be used.

The hydrogen partial pressure applied during step (i) preferably lies in the range from equal to or more than 1.0 Megapascal (MPa), preferably equal to or more than 2.0 MPa, more preferably equal to or more than 3.0 MPa to equal to or less than 16.0 MPa, preferably equal to or less than 12.0 MPa, more preferably equal to or less than 8.0 MPa. All pressures herein are absolute pressures.

The total pressure applied during the reaction is suitably at least 1.0 MPa, preferably at least 2.0 MPa, more preferably at least 3.0 MPa. The total pressure applied during the reaction is suitably at most 16.0 MPa, more preferably at most 10.0 MPa. Preferably the reactor is pressurized with hydrogen before addition of any starting material. The person skilled in the art will understand that the pressure at 20° C. will be lower than the actual pressure at the reaction temperature. The pressure applied during the reaction when converted back to 20° C., preferably equals a pressure in the range from equal to or more than 0.7 MPa to equal to or less than 8.0 MPa.

As explained before, the total pressure may be applied by hydrogen gas or a hydrogen-containing gas, optionally in combination with the partial pressures of the contents of the reaction mixture.

It is preferred to maintain the partial hydrogen pressure at the reaction temperature within such range from 1.0 MPa to 16.0 MPa, preferably during the entire reaction. Therefore hydrogen or a hydrogen-containing gas is preferably introduced into the reaction mixture during reaction as explained above.

During the reaction the carbohydrate source can suitably be contacted with the hydrogen and the hydrogen may suitably be consumed. Hence, when reacting at least a portion of the carbohydrate source with hydrogen, the hydrogen is preferably supplemented.

If the process is a continuous or semi-continuous process, the hydrogen is preferably supplied in a continuous or semi-continuous manner.

In the reactor at least a portion of the carbohydrate source is reacted in the presence of the hydrogen, or with the hydrogen, at a temperature in the range from equal to or more than 170° C. to equal to or less than 270° C. More preferably a temperature in the range from equal to or more than 200° C. to equal to or less than 250° C. is applied. The reactor may be brought to a temperature within these ranges before addition of any starting material and can be maintained at a temperature within the range.

As indicated above, without wishing to be bound to any theory it is believed that in the environment that is created in the reaction zone, hexavalent tungsten compounds and pentavalent tungsten compounds may exist and that it may be these tungsten species that are effective in attacking the carbon-carbon bonds in saccharides to form alkylene glycol precursors. It is further believed that both the hexavalent and the pentavalent tungsten compounds may deposit, for example by adsorption, onto the surface of the heterogeneous catalyst and may thereby inactivate the heterogeneous catalyst.

Aiqin Wang et al., in their article titled "One-Pot Conversion of cellulose to Ethylene Glycol with Multifunctional Tungsten-Based Catalysts" published in Accounts of Chemical Research (2013), vol. 46, pages 1377 to 1386, describes a one-pot catalytic conversion of cellulose to ethylene glycol. Aiqin Wang et al. suggest that when using tungsten compounds in combination with a hydrogenation catalyst such as Ni and Ru, dissolved $H_xWO_3$ is the genuinely catalytically active species for C—C cleavage, and the reaction for C—C cleavage of cellulose proceeds through a homogeneous catalysis pathway.

Without wishing to be bound by any kind of theory the present inventors believe that the active species for the cleavage part of the hydrogenolysis reaction may actually comprise a complex of hexavalent tungsten and pentavalent tungsten. It is believed that hexavalent tungsten may adsorb at the surface of the heterogeneous catalyst, and especially the transition metal thereof, and is reduced to the pentavalent tungsten, which pentavalent tungsten subsequently may desorb again from the surface. In solution subsequently a $H_xW_3O_{10}$ species may be formed, a complex of hexavalent tungsten and pentavalent tungsten. The heterogeneous catalyst, comprising one or more materials selected from transition metals from groups 8, 9 and 10 of the Periodic Table of the Elements, may therefore have two functions: (i) catalyzing the hydrogenation of the mentioned alkylene glycol precursors to alkylene glycol; and (ii) catalyzing the reduction of hexavalent tungsten to pentavalent tungsten.

The present inventors have found that, if operated for a prolonged period of time an increased amount of tungsten species can become deposited onto the surface of the heterogeneous catalyst, and especially the transition metal thereof, increasingly preventing the heterogeneous catalyst from catalyzing the hydrogenation of the mentioned alkylene glycol precursors to alkylene glycol, resulting in a decrease in selectivity towards ethylene glycol. Such tungsten species may become adsorbed, may become complexed or may in another manner become deposited onto the surface of the transition metal.

Hence, by reacting carbohydrates in the presence of hydrogen in the process according to the invention, not only ethylene glycol is produced, but also spent heterogeneous catalyst is generated, which spent heterogeneous catalyst is believed to be enriched in deposited tungsten species.

The molar ratio of moles tungsten to moles transition metal, all calculated as metal, of the spent heterogeneous catalyst withdrawn from the reactor may thus, suitably on average, be higher than the molar ratio of moles tungsten to moles transition metal, all calculated as metal, of the heterogeneous catalyst that was introduced to the reactor. For example, when a slurry of heterogeneous catalyst is provided to a continuously stirred tank reactor (CSTR), the heterogeneous catalyst withdrawn from such CSTR (i.e. the spent heterogeneous catalyst in such a case) is believed to contain, suitably on average, a higher amount of tungsten species deposited onto its surface than the heterogeneous catalyst that was provided to the CSTR.

When a plug flow reactor is used comprising a fixed bed of heterogeneous catalyst, the heterogeneous catalyst after use in the reaction (i.e. the spent heterogeneous catalyst in such a case) is believed to contain, suitably on average, a higher amount of tungsten species deposited onto its surface than the heterogeneous catalyst with which the use was started.

After the reaction of at least a portion of the carbohydrate source, a reactor product stream can be withdrawn from the reactor. This reactor product stream suitably contains the ethylene glycol (ethane-1,2-diol) yielded by the reaction. In addition, the reactor product stream can contain other compounds, such as unreacted carbohydrate source and one or more by-products such as diethylene glycol (2,2'-oxydi (ethan-1-ol)) propylene glycol (propane-1,2-diol and/or propane-1,3-diol), glycerol (propane-1,2,3-triol), butane-1,2-diol, butane-1,3-diol, butane-2,3-diol, butane-1,4-diol, methanol, ethanol, propanol, butanol, sorbitol (hexane-1,2,3,4,5,6-hexol) and/or erythritol (butane-1,2,3,4-tetraol). Propylene glycol can be an economically interesting by-product and may also be considered a product.

Step (ii) suitably comprises regenerating the spent heterogeneous catalyst by removing at least a portion of deposited tungsten species from the spent heterogeneous catalyst. Step (ii) suitably yields a regenerated heterogeneous catalyst.

Step (ii) is preferably carried out in the absence or essential absence of hydrogen.

The regeneration can be carried out in any manner known by a person skilled in the art to remove tungsten species from a catalyst.

More preferably, at least a portion of the deposited tungsten species is removed from the spent heterogeneous catalyst by washing of the spent heterogeneous catalyst with a washing liquid. Such washing suitably yields a washed, regenerated, heterogeneous catalyst.

The washing liquid preferably comprises or consists of an alkylene glycol, glycerol or other polyol, an alkali metal hydroxide solution or an alkali earth metal hydroxide solution or a combination of any of these. Preferably such washing liquid is chosen from the group consisting of alkylene glycols, a mixture of water and alkylene glycol, glycerol, a mixture of water and glycerol, an alkali metal hydroxide solution or an alkali earth metal hydroxide solution. More preferably the washing liquid is an alkylene glycol or a mixture of alkylene glycol and water. Examples of suitably alkylene glycols are ethylene glycol, propylene glycol and butylene glycol. Most preferably the washing liquid comprises or consists of ethylene glycol, propylene glycol, butylene glycol or a mixture thereof, such as an ethylene glycol/propylene glycol mixture, an ethylene glycol/butylene glycol mixture or an propylene glycol/butylene glycol mixture.

The washing liquid preferably contains no, or essentially no, tungsten species.

Preferred alkali metal hydroxide solutions include aqueous solutions of sodium hydroxide, potassium hydroxide and combinations thereof. An aqueous solution of sodium hydroxide is most preferred.

The washing can be carried out at a wide range of temperatures. Preferably, the washing of the spent heterogeneous catalyst is carried out at a temperature (herein also referred to as the "washing temperature") in the range from equal to or more than 100° C., more preferably equal to or more than 150° C., still more preferably equal to or more than 170° C., and most preferably equal to or more than 180° C., to equal to or less than 300° C., more preferably equal to or less than 250° C. and most preferably equal to or less than 230° C.

The amount of washing liquid applied may vary widely. Preferably the volume of washing liquid applied per weight of catalyst ranges from equal to or more than 2 ml washing liquid per gram of catalyst (2 ml/gram) to equal to or less than 500 ml washing liquid per gram of catalyst (500 ml/gram). More preferably the volume of washing liquid applied per weight of catalyst ranges from equal to or more than 10 ml/gram to equal to or less than 100 ml/grams.

In order to achieve optimal results, it can be advantageous to sequentially apply two or more portions, more preferably 2 to 5 portions, of washing liquid. That is, preferably the washing of the spent heterogeneous catalyst comprises two or more, more preferably 2 to 5, washing steps. Preferably each washing step would include washing of the spent heterogeneous catalyst with a washing liquid and optionally subsequent drying of the washed spent heterogeneous catalyst. After washing and drying a subsequent washing step could then be initiated. It can also be advantageous to wash the spent heterogeneous catalyst in a continuous manner by applying a continuous stream of washing liquid to the spent heterogeneous catalyst.

If two or more portions of washing liquid are applied, it is possible to use one and the same type of washing liquid for each portion, but one could also use different types of washing liquid for different portions or washing liquids with different concentrations for different portions. It can be advantageous to use a combination of washing liquids. For example the heterogeneous catalyst can first be washed with one washing liquid and can subsequently be washed with another, different washing liquid.

The time during which the catalyst is washed (also herein referred to as the "washing time"), can also vary widely. Good results can already be achieved when a washing time of 1 hour is used. Preferably the washing of the spent heterogeneous catalyst is carried out whilst applying washing times in the range from equal to or more than 15 minutes to equal to or less than 16 hours, more preferably in the range from equal to or more than 0.5 hour to equal to or less than 12 hours, and most preferably in the range from equal to or more than 1 hour to equal to or less than 8 hours.

Drying of the, suitably washed and/or regenerated, heterogeneous catalyst can be carried out in a wide variety or ways.

The drying can for example include the application of heat and/or the application of a vacuum and/or the application of an inert gas. Preferably the washed and/or regenerated catalyst is dried under an inert atmosphere, preferably under a flow of nitrogen gas, by applying a temperature in the range from equal to or more than 100° C., more preferably equal to or more than 150° C., still more preferably equal to or more than 170° C., and most preferably equal to or more than 180° C., to equal to or less than 300° C., more preferably equal to or less than 250° and most preferably equal to or less than 230° C.

Preferably therefore step (ii) comprises or consists of:
washing the spent heterogeneous catalyst with a washing liquid, for example with a washing liquid as described herein, to yield a washed, regenerated, heterogeneous catalyst;
drying the washed, regenerated, heterogeneous catalyst, preferably under an inert atmosphere, more preferably under a flow of inert gas, such as nitrogen gas, preferably by applying a temperature in the range from equal to or more than 100° C. to equal to or less than 300° C., to yield a dried, regenerated, heterogeneous catalyst.

Suitably the dried, regenerated, heterogeneous catalyst can be kept under an inert gas flow, such as a nitrogen flow, at room temperature (about 20° C.) until re-use and/or recycling thereof.

Step (ii) can be carried out "in-situ" (i.e. inside the reactor) or "ex-situ" (i.e. outside the reactor).

If the regeneration is carried out "in-situ", at least a portion of the deposited tungsten species is removed from the spent heterogeneous catalyst inside the reactor. This may be the preferred method if the heterogeneous catalyst is present in an immobilized manner, for example if the heterogeneous catalyst is present in the reactor in a fixed bed. In such a case removing deposited tungsten species from the spent heterogeneous catalyst preferably comprises in-situ washing of the spent heterogeneous catalyst. The washing can be carried out intermittently, for example by alternating between a stream containing carbohydrate source and a stream comprising a washing liquid as described above. For example, a plurality of two or more reactors may be operated in swing-mode where, at any one time, one or more reactors are operated in a reaction mode where carbohydrate source is reacted, whilst in one or more other reactors deposited tungsten species are removed from the spent heterogeneous catalyst, for example by washing.

The regeneration can also be carried out "ex-situ". This may be the preferred method where the reactor is a slurry reactor, an ebulated bed reactor, a fluidized bed reactor, a bubble reactor, an external recycle loop reactor or a continuously stirred tank reactor. For example, the regeneration in step (ii) can comprise:
recovering at least a portion of the spent heterogeneous catalyst from the reactor;
removing at least a portion of deposited tungsten species from the spent heterogeneous catalyst to thereby produce a regenerated heterogeneous catalyst;
recycling at least a portion of the regenerated heterogeneous catalyst to the reactor.

The spent heterogeneous catalyst can be recovered from the reactor batchwise, or in a continuous or intermittent manner. The spent heterogeneous catalyst can be included in a reactor product stream or it can be withdrawn or unloaded from the reactor via a separate stream.

Preferably step (ii) comprises
recovering periodically or continuously at least a portion of the spent heterogeneous catalyst from the reactor;
removing periodically or continuously at least a portion of deposited tungsten species from such spent heterogeneous catalyst to thereby produce a regenerated heterogeneous catalyst;
recycling periodically or continuously at least a portion of the regenerated heterogeneous catalyst to the reactor.

The spent heterogeneous catalyst can be recovered from the reactor in any manner known by a person skilled in the art. All or merely a portion of the spent heterogeneous catalyst present can be recovered. In a continuous process, preferably a portion of the spent heterogeneous catalyst is continuously removed.

If the spent heterogeneous catalyst is withdrawn from the reactor as a slurry in a liquid, the spent heterogeneous catalyst can subsequently be separated from such slurry for example by sedimentation, decantation, filtration and/or centrifugation. Any electrolytes which may be present may be removed with the help of one or more ion exchange resins.

Subsequently a portion or all of the deposited tungsten species can be removed from the spent heterogeneous catalyst.

Preferably any ex-situ washing of the spent heterogeneous catalyst with a washing liquid is carried out by suspending or slurrying the spent heterogeneous catalyst in the washing liquid. Preferably such washing liquid-heterogeneous catalyst suspension or slurry contains in the range from equal to or more than 10 grams/liter to equal to or less than 500 grams/liter of heterogeneous catalyst. In order to speed up the washing process such suspension or slurry can be agitated or mixed, for example by stirring. Such mixing, respectively stirring, can be carried out batch-wise, semi-continuously or continuously. For example, the washing of the spent heterogeneous catalyst with a washing liquid may conveniently be carried out with the help of a dynamic or static mixer. Preferably such suspension or slurry of the spent heterogeneous catalyst in washing liquid is stirred, for example at a speed in the range from equal to or more than 20 to equal to or less than 2000 rounds per minute. Preferences for the washing liquid, washing temperature and washing time are as described above.

Step (ii) suitably yields a regenerated heterogeneous catalyst. The regenerated heterogeneous catalyst may still comprise some residual tungsten deposited onto the transition metal. The tungsten species remaining in the regenerated heterogeneous catalyst are preferably tungsten species wherein the tungsten has an oxidation state of +4, +5 and/or +6. More preferably the tungsten species contain or consist of tungsten dioxide (also known as tungsten (IV) oxide) and/or tungsten trioxide (also known as tungsten (VI) oxide). That is, suitably the regenerated heterogeneous catalyst comprises remaining tungsten dioxide and/or tungsten trioxide deposited onto the transition metal(s). The average weight percentage of tungsten, calculated as metal, of such regenerated heterogeneous catalyst, however, may suitably be lower than the average weight percentage of tungsten, calculated as metal, of the spent heterogeneous catalyst.

More suitably the weight ratio of total amount of tungsten species (calculated on tungsten metal basis) to transition metal (calculated on metal basis) in the regenerated heterogeneous catalyst is lower than the weight ratio of total amount of tungsten species (calculated on tungsten metal basis) to transition metal (calculated on metal basis) in the spent heterogeneous catalyst. Preferably the weight ratio of weight tungsten to the total weight of transition metal, all calculated on metal basis, in the regenerated heterogeneous catalyst is equal to or lower than 30:1, more preferably equal to or lower than 20:1, even more preferably equal to or lower than 10:1, still more preferably equal to or lower than 5:1 (wt/wt), and most preferably equal to or lower than 2:1 (wt/wt). Suitably the weight ratio of weight tungsten to the total weight of transition metal, all calculated on metal basis, in the regenerated heterogeneous catalyst is equal to or higher than 1:1000, more suitably equal to or higher than 1:100.

As illustrated by the examples, such regenerated heterogeneous catalyst may under certain circumstances even perform better in step (i) than a fresh heterogeneous catalyst. The regenerated heterogeneous catalyst is therefore believed to be novel and inventive in itself.

The present invention therefore also provides a heterogeneous catalyst composition containing:
- one or more transition metals from groups 8, 9 and 10 of the Periodic Table of the Elements, supported on a carrier; and
- one or more tungsten species deposited onto the transition metal(s).

Preferences for the transition metal are as described herein above. Preferably the heterogeneous catalyst composition comprises ruthenium and/or nickel. More preferably the transition metal is ruthenium or nickel. Preferences for the carrier are as described herein above. Preferably such carrier comprises carbon or activated carbon. The tungsten species are preferably tungsten species wherein the tungsten has an oxidation state of +4, +5 and/or +6. More preferably the tungsten species contain or consist of tungsten dioxide (also known as tungsten (IV) oxide) and/or tungsten trioxide (also known as tungsten (VI) oxide). That is, preferably the heterogeneous catalyst composition comprises tungsten dioxide and/or tungsten trioxide deposited onto the transition metal(s). Preferably the novel heterogeneous catalyst composition comprises in the range from equal to or more than 1.0 wt. %, more preferably equal to or more than 2.0 wt. %, still more preferably equal to or more than 5.0 wt. %, to equal to or less than 50.0 wt. %, more preferably equal to or less than 20.0 wt. %, of transition metal, on the basis of the total weight of transition metal and carrier. If a feed stream to the reactor is used containing in the range of equal to or more than 20.0 wt. % of carbohydrate source, based on the total weight of the carbohydrate source and solvent, preferably a heterogeneous catalyst is used comprising in the range of equal to or more than 5.0 wt. %, more preferably equal to or more than 10.0 wt. %, to equal to or less than 50.0 wt. %, more preferably equal to or less than 20.0 wt. % of transition metal, on the basis of the total weight of transition metal and carrier, is used. It is believed that such a higher loading of transition metal can advantageously assist to convert a feedstream with a higher concentration of carbohydrate source.

Preferably the weight ratio of weight tungsten to the total weight of transition metal, all calculated on metal basis, in the novel heterogeneous catalyst composition is equal to or lower than 30:1, more preferably equal to or lower than 20:1, even more preferably equal to or lower than 10:1, still more preferably equal to or lower than 5:1 (wt/wt), and most preferably equal to or lower than 2:1 (wt/wt). Suitably the weight ratio of weight tungsten to the total weight of transition metal, all calculated on metal basis, in novel heterogeneous catalyst composition is equal to or higher than 1:1000, more suitably equal to or higher than 1:100.

Step (iii) suitably comprises using at least a portion of the regenerated heterogeneous catalyst as heterogeneous catalyst in the reaction of step (i).

The regenerated heterogeneous catalyst can be recycled to step (i) in any manner known to be suitable by a person skilled in the art. For example the regenerated heterogeneous catalyst can be mixed with fresh heterogeneous catalyst and suspended and/or slurried in a solvent, such as the solvents described above for step (i).

Preferably in the range from equal to or more than 1 wt. %, more preferably equal to or more than 5 wt. %, most preferably equal to or more than 10 wt. % and equal to or less than 100 wt. %, more preferably equal to or less than 95 wt. % of the regenerated heterogeneous catalyst is recycled to step (i).

Preferably, step (i) therefore comprises reacting, in a reactor, at a temperature in the range from equal to or more than 170° C. to equal to or less than 270° C., at least a portion of a carbohydrate source in the presence of hydrogen; a solvent; a homogeneous catalyst, which homogeneous catalyst contains tungsten; and in the presence of:
- (a) a heterogeneous catalyst, which heterogeneous catalyst contains one or more transition metals from groups 8, 9 and 10 of the Periodic Table of the Elements and which heterogeneous catalyst contains no or essentially no tungsten (this heterogeneous catalyst can herein also be referred to as fresh or virgin heterogeneous catalyst); and/or
- (b) a regenerated heterogeneous catalyst, which regenerated heterogeneous catalyst contains tungsten and one or more transition metals from groups 8, 9 and 10 of the Periodic Table of the Elements. More preferably the regenerated heterogeneous catalyst contains tungsten species deposited onto the transition metal(s). Further preferences for the regenerated heterogeneous catalyst are as described above for the novel heterogeneous catalyst composition.

More preferably, step (i) is preferably carried out in the presence of both:
- (a) a heterogeneous catalyst, which heterogeneous catalyst contains one or more transition metals from groups 8, 9 and 10 of the Periodic Table of the Elements and which heterogeneous catalyst contains no or essentially no tungsten (this heterogeneous catalyst can herein also be referred to as fresh or virgin heterogeneous catalyst); and
- (b) a regenerated heterogeneous catalyst, which regenerated heterogeneous catalyst contains tungsten and one or more transition metals from groups 8, 9 and 10 of the Periodic Table of the Elements. More preferably the regenerated heterogeneous catalyst contains tungsten species deposited onto the transition metal(s).

Figure 1:
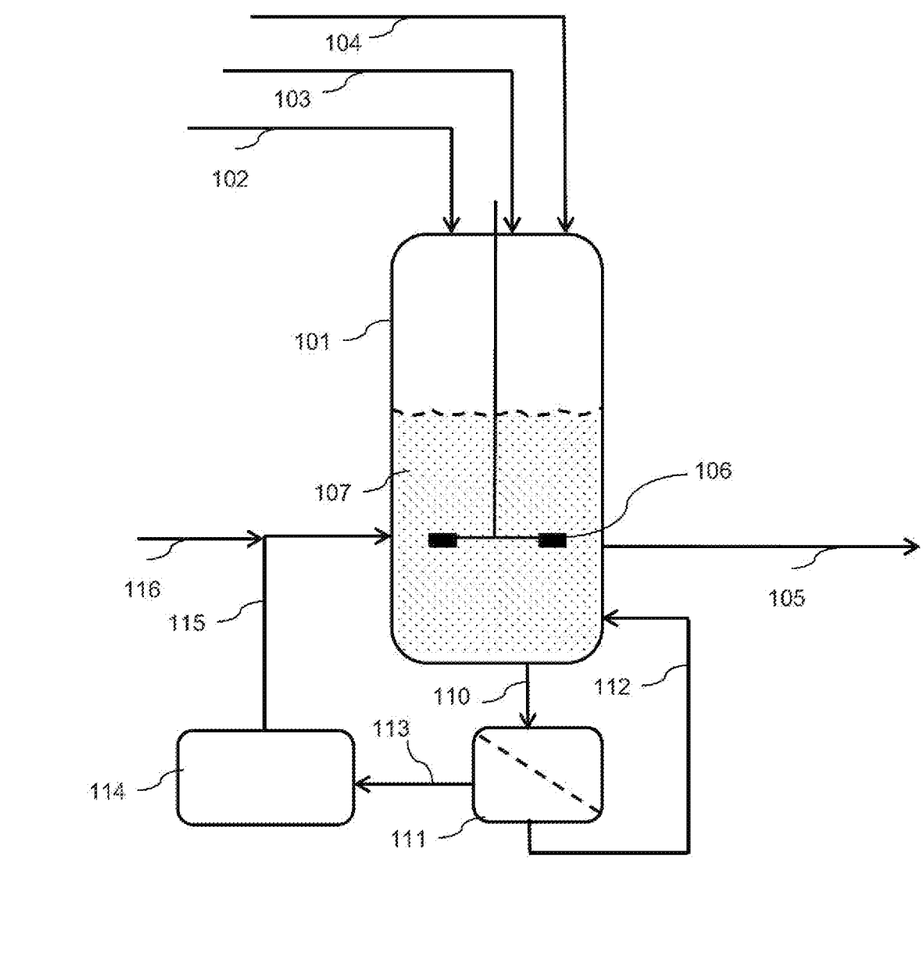
FIG. 1 shows a process according to the invention operated in a continuously stirred tank reactor with an ex-situ removal of deposited tungsten species from the spent heterogeneous catalyst to generate a regenerated heterogeneous catalyst and a recycle of regenerated heterogeneous catalyst.

The process is illustrated by non-limiting FIG. 1.

In the FIGURE a process is illustrated wherein ethylene glycol is produced in a continuously stirred tank reactor (101). The continuously stirred tank reactor (101) is operated at a temperature of 220° C., a pressure of 8 MPa and a stirring rate of 500 rounds per minute. A continuous stream (102) of an aqueous 10 wt. % solution of glucose is supplied to the continuously stirred tank reactor (101). In addition a continuous stream (103) of an aqueous tungsten-containing homogeneous catalyst solution comprising 0.15 wt. % tungstic acid and 19 wt. % of glycerol was added, which aqueous homogeneous catalyst solution was adjusted to a pH of 7 by the addition of sodium hydroxide. As a result of the addition of sodium hydroxide, sodium tungstate is formed. Further a continuous stream (104) of hydrogen, supplied at a rate of 100 normal milliliters per minute, was provided to the continuously stirred tank reactor (101).

In the reactor, the glucose is converted to ethylene glycol product and one or more side-products. A product solution containing ethylene glycol and one or more side-products is removed from the reactor via stream (105). The reactor comprises a suspension (107), containing a heterogeneous catalyst suspended in a reaction mixture, which heterogeneous catalyst comprises 5 wt. % ruthenium carried on an activated carbon support. The suspension (107) is stirred with stirrer (106), for example at a rate in the range from 500 to 3000 rounds per minute (rpm).

A portion of the suspension (107) is continuously withdrawn via stream (110) and forwarded to filter unit (111). In filter unit (111), the suspension (107) is filtered and separated into spent heterogeneous catalyst and liquid reaction mixture. The liquid reaction mixture is recycled to the reactor via stream (112). The spent heterogeneous catalyst is forwarded via a screw feed (113) to regeneration unit (114). In regeneration unit (114) the spent heterogeneous catalyst is dried and washed 3 times with a 50/50 wt/wt mixture of ethylene glycol and butylene glycol to thereby generate a stream of regenerated heterogeneous catalyst suspended in 50/50 wt/wt mixture of ethylene glycol and butylene glycol. The suspended regenerated heterogeneous catalyst is recycled via stream (115) to the continuously stirred tank reactor (101). Optionally additional fresh heterogeneous catalyst is added via make-up stream (116).

The process is herein below further illustrated by the following non-limiting examples.

EXAMPLES 1-13 AND COMPARATIVE EXAMPLE A

A spent heterogeneous catalyst, comprising ruthenium on activated carbon, was obtained from a reaction of glucose to ethylene glycol in the presence of hydrogen, a homogeneous tungsten-containing catalyst and a heterogeneous catalyst comprising 5 wt. % ruthenium on activated carbon catalyst (i.e. 5 wt. % Ru/AC) in a continuously stirred tank reactor at a temperature of about 220° C. The spent heterogeneous catalyst was isolated and subsequently dried before being used in the examples as listed below.

In comparative example A, the spent heterogeneous catalyst was not washed.

For each of the examples 1-13 and comparative example A about 1.0 grams of the dried spent heterogeneous catalyst was weighed into a round bottom flask. Hereafter an amount in milliliters (ml) of washing liquid as summarized in Table 1 was added per gram (g) of spent heterogeneous catalyst, and the spent heterogeneous catalyst was suspended in the washing liquid. In example 2 an aqueous solution of sodium hydroxide (NaOH/water) was used in a molar ratio of sodium to tungsten (Na:W) of 2:1.

The suspension was heated to a temperature as summarized in Table 1 and stirred for a number of hours as summarized in Table 1. Evaporation of the washing liquid was prevented by a reflux set-up. Each suspension was stirred at a speed of 500 rounds per minute (rpm).

Subsequently the suspension was cooled and filtered over a 1 micrometer (µm) glass filter using a Buchner funnel (Whatmann glass microfiber filter cat no. 1821-042) and a solid residue was obtained. The solid residue remaining on the filter was washed with 500 ml ultrapure water (MilliQ). Subsequently the obtained solid residue was dried overnight at 70° C. under vacuum in a vacuum oven. The tungsten and ruthenium content and the weight ratio of tungsten to ruthenium in the washed and dried solid residue was determined by Inductively coupled Plasma (ICP) analysis and summarized in Table 1. The weight percentages as listed in Table 1 are based on the total weight of the solid residue. The skilled person will therefore understand that when the relative weight percentage of tungsten metal increases, the total weight of the solid residue may increase and hence the relative weight percentage of ruthenium may decrease, even where the absolute amount of ruthenium actually remains equal.

As illustrated by examples 1 and 2, the difference between the aqueous sodium hydroxide solution and the glycerol as washing solvents was relatively small, but glycerol was more effective. From the initial about 48 wt. % tungsten, about 19 wt. % was left after washing with glycerol. When using the aqueous sodium hydroxide solution as washing solvent, about 22 wt. % remained.

Economically, it would be beneficial to use a (side) product stream from the process, such as an 90:10 wt/wt ethylene glycol/propylene glycol (EG/PG) mixture, as washing solvent. As illustrated by examples 3 to 7, such a side product stream can be very effective as a washing solvent. In all cases, the tungsten content of the dried spent heterogeneous catalyst after washing with EG/PG was lower than when this catalyst was washed with an aqueous sodium hydroxide solution or glycerol. The experiment at 4 hrs and 50 g/l with EG/PG solvent resulted in a tungsten content of about 14 wt. % compared to about 22 wt. % and about 19 wt. % with aqueous sodium hydroxide solution and glycerol respectively.

Another (side) product stream from the process can be a 50:50 wt/wt ethylene glycol/butylene glycol azeotrope (EG/BG) mixture. As illustrated by examples 8 to 14 and especially when comparing examples 1, 2, 3 and 8 and 9, it can be found that such an ethylene glycol/butylene glycol mixture was the most effective washing liquid.

As illustrated in Table 1, the washing time and amount of washing liquid per gram of catalyst were also varied. As illustrated by examples 3, 4 and 5, when the washing time was extended to 6 hours, the tungsten content dropped significantly independent of the washing liquid to catalyst ratio. A shorter washing time generally resulted in a higher tungsten content although this was not the case when the washing liquid to catalyst ratio was lowered.

TABLE 1

| Ex. | Washing liquid | Washing time (hrs) | Washing temperature (° C.) | Washing liquid per gram catalyst (ml/g) | Residual W (wt. %) | Residual Ru (wt. %) | Weight ratio W/Ru |
|---|---|---|---|---|---|---|---|
| A* | None | n.a. | n.a. | n.a. | 48.0 | 1.5 | 31.8 |
| 1 | Glycerol | 4 | 200 | 50 | 19.3 | 3.0 | 6.5 |

TABLE 1-continued

| Ex. | Washing liquid | Washing time (hrs) | Washing temperature (° C.) | Washing liquid per gram catalyst (ml/g) | Residual W (wt. %) | Residual Ru (wt. %) | Weight ratio W/Ru |
|---|---|---|---|---|---|---|---|
| 2 | NaOH/water | 4 | 200 | 50 | 22.2 | 3.1 | 7.1 |
| 3 | EG/PG (90/10) | 4 | 200 | 50 | 13.5 | 3.5 | 3.8 |
| 4 | EG/PG (90/10) | 6 | 200 | 100 | 4.4 | 3.8 | 1.2 |
| 5 | EG/PG (90/10) | 6 | 200 | 33.3 | 4.4 | 3.8 | 1.2 |
| 6 | EG/PG (90/10) | 2 | 200 | 50 | 16.8 | 3.2 | 5.3 |
| 7 | EG/PG (90/10) | 2 | 200 | 33.3 | 11.0 | 3.6 | 3.1 |
| 8 | EG/BG (50/50) | 4 | 200 | 50 | 5.9 | 3.9 | 1.5 |
| 9 | EG/BG (50/50) | 4 | 200 | 50 | 7.3 | 3.8 | 1.9 |
| 10 | EG/BG (50/50) | 1 | 200 | 50 | 15.6 | 3.5 | 4.5 |
| 11 | EG/BG (50/50) | 2 | 200 | 10 | 15.7 | 3.1 | 5.1 |
| 12 | EG/BG (50/50) | 4 | 200 | 10 | 14.5 | 3.2 | 4.6 |
| 13 | EG/BG (50/50) | 16 | 200 | 10 | 14.2 | 3.0 | 4.7 |

*Comparative example

EXAMPLES 14-19 AND COMPARATIVE EXAMPLES B AND C

The washed and dried solid residues obtained in examples 1 to 13 exemplify regenerated heterogeneous catalysts.

To test these regenerated heterogeneous catalysts, an equivalent amount of regenerated catalyst from examples 1, 3 and 9, corresponding to about 12.5 milligrams (mg) of ruthenium, was weighted into a 6 ml full-liquid continuously stirred tank reactor. A mixture of 10 wt. % glucose, 0.15 wt. % $H_2WO_4$, 0.18 grams/liter NaOH and 19 wt. % glycerol in water was fed continuously with a rate of 0.25 ml/min. The pH of the feed was about 7. The CSTR was operated at a temperature of 220° C. and a pressure of 8 MPa. A hydrogen flow of 100 normal milliliters per minute (Nml/min) was applied. (Normal liters per minute reflect the liters per minute corrected to standardized conditions of a temperature of 0° C. and an absolute pressure of 1 atmosphere (corresponding to 0.101 MPa)).

From the reactor effluent a sample was taken at about 90 minutes of runtime and at about 240 minutes of runtime and analyzed by liquid chromatography (LC). The results are summarized in table 2.

As a comparison the same test was carried out with a fresh heterogeneous catalyst, comprising 5 wt. % ruthenium on activated carbon and no tungsten. (see comparative examples B and C)

A test with non-washed dried spent catalyst of comparative example A was stopped because humins formation was observed.

As illustrated by the results in table 2, the use of regenerated heterogeneous catalysts results in an at least equal, but at least for examples 14 to 17 significantly better, ethylene glycol selectivities. Furthermore the regenerated heterogeneous catalysts can be used for several hours.

The results of table 2 hence illustrate that when spent heterogeneous catalyst is regenerated by removing at least a portion of deposited tungsten species from the spent heterogeneous catalyst it can be re-used in a process for producing ethylene glycol. As a result, prolonged runtimes can be achieved.

TABLE 2

| Heterogeneous catalyst | Example | Runtime (min) | Conv % | MassBal % | EG Sel % | PG Sel % |
|---|---|---|---|---|---|---|
| Fresh catalyst comprising 5 wt. % ruthenium on activated carbon | B* | 90 | 100.0 | 80.4 | 52.9 | 13.8 |
| | C* | 242 | 100.0 | 77.7 | 58.7 | 11.3 |
| Regenerated catalyst of example 9 (washed with EG/BG) | 14 | 90 | 99.8 | 91.3 | 67.8 | 12.1 |
| | 15 | 243 | 100.0 | 90.4 | 70.9 | 10.2 |
| Regenerated catalyst of example 3 (washed with EG/PG) | 16 | 90 | 99.4 | 96.2 | 72.6 | 10.0 |
| | 17 | 240 | 100.0 | 87.8 | 68.4 | 11.3 |
| Regenerated catalyst of example 1 (washed with Glycerol) | 18 | 90 | 99.7 | 71.9 | 53.6 | 9.4 |
| | 19 | 245 | 99.9 | 82.4 | 65.1 | 7.8 |

*Comparative example
**A test with non-washed dried spent catalyst of comparative example A was stopped because humins formation was observed.

The invention claimed is:

1. A process for the production of ethylene glycol including the steps of:
   (i) reacting, in a reactor, at a temperature in the range from equal to or more than 170° C. to equal to or less than 270° C., at least a portion of a carbohydrate source in the presence of hydrogen, a solvent, a homogeneous catalyst, which homogeneous catalyst contains tungsten, and a heterogeneous catalyst, which heterogeneous catalyst contains one or more transition metals selected from groups 8, 9 and 10 of the Periodic Table of the Elements, yielding ethylene glycol and a spent heterogeneous catalyst;
   (ii) regenerating the spent heterogeneous catalyst by removing at least a portion of deposited tungsten species from the spent heterogeneous catalyst, yielding a regenerated heterogeneous catalyst; and
   (iii) using at least a portion of the regenerated heterogeneous catalyst as heterogeneous catalyst in the reaction of step (i);
   wherein at least a portion of the deposited tungsten species is removed from the spent heterogeneous catalyst by washing of the spent heterogeneous catalyst with a washing liquid, wherein the washing liquid comprises ethylene glycol, propylene glycol, butylene glycol or a mixture thereof.

2. The process according to claim 1, wherein the homogeneous catalyst contains tungsten which tungsten is present as a tungsten compound or tungsten derived from a tungsten compound.

3. The process according to claim 1, wherein the homogeneous catalyst contains recycled tungsten species recovered, directly or indirectly, from the effluent of the reactor.

4. The process according to claim 1, wherein the homogeneous catalyst contains or consists of a complex of hexavalent tungsten and pentavalent tungsten.

5. The process according to claim 1, wherein the molar ratio of moles tungsten to moles transition metal, all calculated as metal, of the spent heterogeneous catalyst is higher than the molar ratio of moles tungsten to moles transition metal, all calculated as metal, of the heterogeneous catalyst as introduced to the reactor.

6. The process according to claim 1, wherein step (ii) comprises:
    washing the spent heterogeneous catalyst with the washing liquid to yield a washed, regenerated, heterogeneous catalyst;
    drying the washed, regenerated, heterogeneous catalyst to yield a dried, regenerated, heterogeneous catalyst.

7. The process according to claim 1, wherein the washing of the spent heterogeneous catalyst with the washing liquid is carried out at a temperature in the range from equal to or more than 150° C. to equal to or less than 250° C.

8. The process according to claim 1, wherein the washing of the spent heterogeneous catalyst comprises two or more washing steps.

9. The process according to claim 1, wherein step (ii) comprises:
    recovering at least a portion of the spent heterogeneous catalyst from the reactor;
    removing at least a portion of deposited tungsten species from the spent heterogeneous catalyst to thereby produce a regenerated heterogeneous catalyst;
    recycling at least a portion of the regenerated heterogeneous catalyst to the reactor.

10. The process according to claim 9, wherein step (ii) comprises:
    recovering periodically or continuously at least a portion of the spent heterogeneous catalyst from the reactor;
    removing periodically or continuously at least a portion of deposited tungsten species from such spent heterogeneous catalyst to thereby produce a regenerated heterogeneous catalyst;
    recycling periodically or continuously at least a portion of the regenerated heterogeneous catalyst to the reactor.

11. The process according to claim 1, wherein step (ii) is carried out in the absence of hydrogen.

12. The process according to claim 1, wherein the tungsten species contain tungsten dioxide and/or tungsten trioxide.

13. The process according to claim 1, wherein the average weight percentage of tungsten, calculated as metal, of the regenerated heterogeneous catalyst is lower than the average weight percentage of tungsten, calculated as metal, of the spent heterogeneous catalyst.

14. The process according to claim 1, wherein step (i) comprises reacting, in a reactor, at a temperature in the range from equal to or more than 170° C. to equal to or less than 270° C., at least a portion of a carbohydrate source,
    in the presence of hydrogen; a solvent; and a homogeneous catalyst, which homogeneous catalyst contains tungsten; and
    in the presence of:
    (a) a heterogeneous catalyst, which heterogeneous catalyst contains one or more transition metals from groups 8, 9 and 10 of the Periodic Table of the Elements and which heterogeneous catalyst contains no or essentially no tungsten; and/or
    (b) a regenerated heterogeneous catalyst, which regenerated heterogeneous catalyst contains tungsten and one or more transition metals from groups 8, 9 and 10 of the Periodic Table of the Elements.

* * * * *